United States Patent [19]

Miura et al.

[11] Patent Number: 4,771,008
[45] Date of Patent: Sep. 13, 1988

[54] METHOD FOR QUANTITATIVE ANALYSIS OF THYROID HORMONE

[75] Inventors: Kenji Miura; Yukio Yasuda, both of Asaka, Japan

[73] Assignee: Fuji Photo Film Co., Ltd., Kanagawa, Japan

[21] Appl. No.: 36,143

[22] Filed: Apr. 6, 1987

Related U.S. Application Data

[63] Continuation of Ser. No. 873,465, Jun. 6, 1986, abandoned, which is a continuation of Ser. No. 518,077, Jul. 28, 1983, abandoned.

[30] Foreign Application Priority Data

Jul. 30, 1982 [JP] Japan .................. 57-132252

[51] Int. Cl.$^4$ .................................. G01N 33/53
[52] U.S. Cl. ......................... 436/500; 435/7; 436/825
[58] Field of Search .............. 436/500, 825; 435/7

[56] References Cited

U.S. PATENT DOCUMENTS 3,911,096 10/1975 Chopra ........................... 436/500
4,238,472 12/1980 Albro et al. ..................... 436/825
4,492,762 1/1985 Wang et al. ..................... 436/825

*Primary Examiner*—Sam Rosen
*Attorney, Agent, or Firm*—Jules E. Goldberg

[57] ABSTRACT

A method for quantitative analysis of low molecular weight components which are contained in a protein-containing liquid sample originating from body fluids and are capable of binding to said protein, characterized by incorporating into the liquid sample a compound having the formula (I):

$$X-(Y)_p-SO_3M \qquad (I)$$

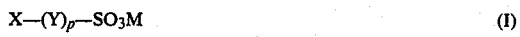

in which M is hydrogen ion, an alkali metal ion, or ammonium ion; X is a straight or branched alkyl, alkenyl, fluorinated alkyl, or fluorinated alkenyl group containing at least 6 carbon atoms, Y is a divilent organic residue; and p is 0 r 1. The compound represented by formula (I) liberates thyroid hormone from bound protein to facilitate analysis.

9 Claims, 2 Drawing Sheets

METHOD FOR QUANTITATIVE ANALYSIS OF THYROID HORMONE

This is a continuation of application Ser. No. 873,465, filed June 6, 1986, now abandoned, which, in turn, is a continuation of application Ser. No. 518,077, filed July 28, 1983, now abandoned.

BACKGROUND OF THE INVENTION

1. Field of the Invention

This invention relates to a method for quantitative analysis of a low molecular weight component contained in a protein-containing liquid sample. More particularly, this invention relates to a method for quantitative analysis of low molecular weight components which are contained in a liquid sample originating from body fluids, such as blood, serum, plasma, urine, bone marrow fluid, saliva, and their processed products, and are capable of binding to proteins contained in the liquid sample.

2. Description of Prior Arts

It is well known that quantitative analysis of a low molecular weight component contained in a liquid sample originating from body fluids is sometimes disturbed by a protein contained together in the liquid sample. This is because most of the low molecular weight components are present in the liquid sample in the form of complexes in which said components are bound to the protein, so that the quantitative analysis utilizing physical or chemical characteristics relating to the free low molecular component is disturbed.

Representative examples of the interaction complex between a low molecular weight component and a protein by which the low molecular weight component is easily bound include an interaction complex between thyroid hormone and albumin, thyroxine-binding-globulin (TGB), or prealbumin.

Quantitative analysis of a thyroid hormone such as thyroxine ($T_4$) present in blood in a trace amount is generally carried out utilizing an antigen-antibody reaction. However, the quantitative analysis of thyroid hormone is ordinarily disturbed because most of the thyroid hormones are present in the liquid sample in the form of complexes in which the thyroid hormones are bound to the proteins such as those described above.

Accordingly, a variety of measures have been employed for keeping the quantitative analysis of a thyroid hormone from disturbance caused by the coexisting protein. Most of measures for eliminating the disturbance caused by the protein utilize addition of an organic solvent to the liquid sample, pH adjustment of the liquid sample, or incorporation of a compound termed "blocker" into the liquid sample. Using one of these measures, the complex between a thyroid hormone and a protein is broken to liberate most of the thyroid hormone, and the so liberated thyroid hormone is then subjected to quantitative analysis.

Among the above-mentioned measures, the incorporation of a blocker has been generally employed because this measure can be easily operated. As the blockers, there are known sodium salicylate, 1-anilino-8-naphthalenesulfonic acid (ANS), and merthiolate (thimerosal).

The incorporation of a blocker into a liquid sample causes separation of the thyroid hormone from the protein under equilibrium hypothetically represented by the following equation.

Accordingly, the method employing the blocker is thought to be a method based on the fact that a blocker incorporated into a liquid sample containing protein-thyroid hormone complexes is predominantly bound to the protein, resulting in liberation of the thyroid hormone.

The method employing a blocker has been generally applied to the quantitative analysis of thyroid hormone based on an antigen-antibody reaction. In more detail, said antigen-antibody reaction of thyroid hormone is carried out on a thyroid hormone liberated in the presence of a blocker.

The thyroid hormone is liberated from the protein in the presence of a blocker according to the above-described equilibrium equation. Thus, it is understood that an increase of the rate of reaction utilized for the quantitative analysis of thyroid hormone, resulting in reducing a period of time required for the analysis, as well as improvement on accuracy of the analysis, is accomplished by placing the equilibrium equation to the right, as far as possible. For this reason, the blocker preferably has a high affinity to the protein so that the blocker can be predominantly bound to the protein. The heretofore known blockers such as sodium salicylate, ANS and thimerosal, however, do not seem satisfactory in their affinity to the protein. Particularly, in a liquid sample containing a high concentration of proteins, these known blockers are poor in their blocking activity, that is, to be predominantly bound to the protein to rapidly liberate the low molecular weight components under analysis.

It is naturally assumed that the poor affinity of the known blocker can be compensated for by incorporating the blocker into the liquid sample in a higher concentration. However, an experimental trial has taught that these known blockers are not satisfactorily effective in the blocking activity in a liquid sample containing a high concentration of proteins, even by using a greater amount of the blocker. Particularly, a solution containing a high concentration of ANS shows a colored phase, and such a color in the solution disturbs the colorimetry or fluorometry to be carried out in a latter stage. Also unfavorable is thimerosal, because the thimerosal contains mercury in the molecule and, when an enzymic reaction is involved in the quantitative analysis, the mercury sometimes disturbs the enzymic reaction.

SUMMARY OF THE INVENTION

A primary object of the present invention is to provide a method for quantitative analysis of low molecular weight components contained in a protein-containing liquid sample, which utilizes a novel blocker having prominently stronger affinity to a variety of proteins than previously known blockers.

Another object of the invention is to provide a method for quantitative analysis of low molecular weight components contained in a protein-containing liquid sample, which utilizes a novel blocker in a relatively high concentration so as to enable to carry out a quantitative analysis with high accuracy even in such a liquid sample as containing a high concentration of proteins.

The present invention provides a method for quantitative analysis of a low molecular weight component which is contained in a protein-containing liquid sample originating from body fluids and is capable of binding to said protein, characterized by incorporating into the liquid sample a compound having the formula (I):

$$X-(Y)_p-SO_3M \qquad (I)$$

in which M is hydrogen ion, an alkali metal ion, or ammonium ion; X is a straight or branched alkyl, alkenyl, fluorinated alkyl, or fluorinated alkenyl group containing at least 6 carbon atoms, Y is a divalent organic residue; and p is 0 or 1.

DESCRIPTION OF PREFERRED EMBODIMENTS

The method of the present invention comprises, in a quantitative analysis of a low molecular weight component contained in a protein-containing liquid sample, incorporating a specific sulfonic acid or sulfonate into the liquid sample, and carrying out the reaction for quantitative analysis of the low molecular weight component in the liquid sample in the presence of the so incorporated sulfonic acid or sulfonate serving as a blocker.

The blocker employed in the present invention is a sulfonic acid, sulfonate or sulfate having the formula (I):

$$X-(Y)_p-SO_3M \qquad (I)$$

In the formula (I), M is hydrogen ion; an alkali metal ion such as sodium ion or potassium ion; or ammonium ion including a quatenary salt of a lower alkylamine; and X is a straight or branched alkyl, alkenyl, fluorinated alkyl, or fluorinated alkenyl group containing at least 6 carbon atoms, preferably 8-22 carbon atoms.

In the formula (I), Y is a divalent organic residue; and p is 0 or 1. Accordingly, there is a case where a divalent organic residue corresponding to Y is not included in the formula (I).

In the case where the formula (I) includes Y, said Y preferably is a divalent organic residue containing a monovalent or divalent aromatic ring. Representative examples of the divalent organic residue include the following residues:

(1)

$$-\text{(aromatic ring)}-O-(CH_2)_m-CH_2\overset{A}{\underset{|}{C}}H-$$

in which the aromatic ring may contain one or more substituents such as hydroxy, alkoxy, aryloxy, alkyl, carbamyl, amido, sulfamido, halogen, carboxyl, and sulfonyl; m is an integer of 0 to 3; and A is hydrogen atom or a lower alkyl group; same hereinbelow (2)

$$-\text{(aromatic ring)}-O-(\overset{A}{\underset{|}{C}}HCH_2O)_m-$$

(3) $-\text{(aromatic ring)}-O-(OCH_2CH_2)_m-$ (4)

$$-\text{(aromatic ring)}-O-(\overset{A}{\underset{|}{C}}HCH_2O)_m-(\overset{D}{\underset{|}{C}}H)_n-$$

in which n is an integer of 1 to 5; and D is hydrogen atom or a lower alkyl group (5) $-\text{(aromatic ring)}-Z-$ in which Z is a simple bonding or a divalent organic residue; same hereinbelow (6) $-NHCO-\text{(aromatic ring)}-Z-$ (7)

$$-\overset{O}{\underset{\|}{C}}O-\text{(aromatic ring)}-Z-$$

(8) $-Z-O-$ (9)

$$-\overset{A}{\underset{|}{C}}ON-\text{(aromatic ring)}-Z-$$

(10) $-NHCONH-\text{(aromatic ring)}-Z-$
(11) $-NHCSNH-\text{(aromatic ring)}-Z-$
(12) $-S-\text{(aromatic ring)}-Z-$
(13) $-O-Z-\text{(aromatic ring)}-$
(14)

$$-\overset{V}{\underset{|}{N}}-Z-\text{(aromatic ring)}-$$

in which V is a monovalent organic residue;

(15)

(16)

$$-\overset{V}{\underset{|}{C}}H-Z-$$

(17)

$$-CO-\overset{V}{\underset{|}{N}}-Z-\text{(aromatic ring)}-$$

, wherein V is the same as above.

Representative examples of the blockers represented by the aforementioned formula (I) include the following compound:

Compounds in which Y is an organic residue corresponding to the above (1) group:

(1a)

(1b)

Compounds in which Y is an organic residue corresponding to the above (2) group:

(2a)

(2b)

Compounds in which Y is an organic residue corresponding to the above (3) group:

(3a)

(3b)

Compounds in which Y is an organic residue corresponding to the above (4) group:

(4a)

(4b)

Compounds in which Y is an organic residue corresponding to the above (5) group:

(5a)

(5b)

Compounds in which Y is an organic residue corresponding to the above (6) group:

(6a)

Compounds in which Y is an organic residue corresponding to the above (7) group:

(7a)

(7b)

Compounds in which Y is an organic residue corresponding to the above (8) group:

(8a)

(8b)

Compounds in which Y is an organic residue corresponding to the above (9) group:

(9a)

(9b)

Compounds in which Y is an organic residue corresponding to the above (10) group:

(10a)

Compounds in which Y is an organic residue corresponding to the above (11) group:

(11a)

Compounds in which Y is an organic residue corresponding to the above (12) group:

(12a)

Compounds in which Y is an organic residue corresponding to the above (13) group:

(13a)

Compounds in which Y is an organic residue corresponding to the above (14) group:

$C_{12}H_{25}NHCH_2CH_2SO_3Na$ (14a)

$\underset{\underset{COCH_3}{|}}{C_{12}H_{25}NCH_2CH_2SO_3Na}$ (14b)

(14c)

Compounds in which Y is an organic residue corresponding to the above (15) group:

(15a)

Compounds in which Y is an organic residue corresponding to the above (16) group:

(16a)

Compounds in which Y is an organic residue corresponding to the above (17) group:

(17a)

Compounds in which p is 0, namely, Y is not included:

$C_8F_{17}$—$SO_3K$ (18a)

$CH_3(CH_2)_{10}CH=CHCH_2$—$SO_3Na$ (18b)

The compounds represented by the aforementioned formula (I) which are employable as blocker in the present invention can be prepared by the processes for the preparation of surface active agents containing —$SO_3M$ group as described in the texts and publications given below, or by processes similar to these processes:

Surface Active Agent (Editions for Synthesitic Process I, II, & III; and Editions for Application I, II, & III), written by Ryohei Oda & Kazuhiro Teramura (Maki Shoten, Japan, 1956):

New Surface Active Agent, written by Hiroshi Horiguchi (Sankyo Shoten, Japan, 1975):

Surfactant Science Series, Vols. 7, 8, 10, & 11, written by Martin J. Schick, Frederick M. Fowkes (Marcel Dekker Inc., N.Y. & Basel, 1976): and McCutcheon's Detergents & Emulsifiers (McCutcheon's Division, Mc Publishing Co., 1979).

Examples of the low molecular weight component to be subjected to the quantitative analysis according to the present invention include hormones such as thyroid hormones, bilirubin, and drugs and their metabolites which are detectable in liquids such as blood, serum, plasma, urine, bone marrow fluid, and saliva taken out of patients having been administered such drugs.

Examples of the drugs include antiepileptics such as phenobarbital, phenytoin, carbamazepine, valproic acid, pyrimidone, ethosuccimide, methosuccimide, and mephenytoin; therapeutic agents for asthma such as theophyline; cardiotonics such as digoxin; antiarrhythmic drugs such as quinidine, lidocaine, procaine amide, N-acetylprocaine amide, and disopyramide; antibiotics such as penicilline, cephalosporin, gentamicin, tobramycin, amikacin, and chloramphenicol; central nervous system stimulants such as amphetamine and ephedrine; and antitumor agents such as methotrexate.

Examples of the liquid sample originating from body fluids include blood, serum, plasma, urine, bone marrow fluid, saliva and their processed products. Examples of proteins contained in these liquid samples include the aforementioned albumin, thyroxine-binding-globulin (TGB), and prealbumin, as well as α-globlin and β-globlin.

The method of the present invention is effectively applied to a quantitative analysis of one or more low molecular weight components such as the above-mentioned hormones and drugs in a liquid sample under conditions where a portion or most of the low molecular weight components are bound to proteins such as above.

The method of the present invention can be carried out in the following manner.

In the first place, if necessary, a buffer agent is added to a liquid sample in which a portion or most of low molecular weight components to be determined are present in the form of complexes with proteins, so as to adjust the liquid sample to pH 6.0–10.5 (approx.). Subsequently, a blocker represented by the aforementioned formula (I) is incorporated into the liquid sample to liberate a portion or most of the low molecular weight components from the proteins. To this liquid sample are further added a protein capable of specifically binding the low molecular weight component, such as an antibody, and a labelled substance such as those that may be the same as the low molecular weight component to be determined and are labelled with a radioactive compound, a fluorescent compound, a fluorescent compound precursor, an enzyme inhibitor, an enzyme substrate, a coenzyme, and an enzyme. A detection of the low molecular weight component is then carried out by detecting quantitatively the amount of a labelled substance in the form of a complex with the antibody or a free labelled substance.

As described hereinbefore, a free low molecular weight component and a low molecular weight component bound by a protein are placed under equilibrium in a liquid sample containing a blocker. Accordingly, in carrying out the detection reaction, a low molecular weight component bound to a protein is gradually liberated from the protein in the course of progress of the detection reaction, because a free low molecular weight component is removed from the solution phase upon formation of a complex with a newly introduced counterpart. For this reason, all of the low molecular weight components contained in the liquid sample, including not only a low molecular weight component having been present originally in a free state, but also a low molecular weight component having been present originally in the form of a complex with a protein can respond to the detection reaction.

The quantitative determination of the low molecular weight component contained in the liquid sample can be easily done, for instance, by comparing the measured value with a calibration curve previously prepared using liquids containing predetermined amounts of the same low molecular weight component at different levels.

The amount of a blocker represented by the formula (I) to be incorporated into the liquid sample for carrying out the above-described detection reaction, depends upon the amounts of proteins and the amount of the low molecular weight component under analysis contained in the liquid sample. Ordinarily, the blocker is incorporated into the liquid sample in an amount of not more than 5% by weight, and more specifically in an amount of 0.01–2% by weight.

As described hereinabove, a blocker represented by the aforementioned formula (I) shows a prominently high blocking activity in comparison with the conventionally employed blockers do, when employed in a method for quantitative analysis of a low molecular weight component which is contained in a protein-containing liquid sample originating from body fluids and is capable of being bound by the protein. Further, a blocker represented by the formula (I) shows satisfactory high blocking activity even in a liquid sample containing a high concentration of proteins. Furthermore, a blocker represented by the formula (I) is highly soluble in a liquid sample, brings about no or little coloring in a liquid sample even in a high concentration, and never disturbs a detection reaction generally utilized for quantitative analysis of low molecular weight components.

The present invention is further described by the following examples, in which the reagents employed were prepared by the procedures given below.

A. Preparation of Fluoresceine-Labelled Thyroxine (FITC-Gly-T$_4$)

(1) Preparation of t-butoxycarbonylglycyl thyroxine methyl ester (Boc-Gly-T$_4$-OCH$_3$)

In 5 ml. of tetrahydrofuran (THF), 329 mg. (1.21 mmol.) of t-butoxycarbonylglycine succinyl ester (Boc-Gly-OSu) was dissolved. Independently, 1.0 g. (1.21 mmol.) of thyroxine methyl ester hydrochloride was dissolved in 15 ml. of THF, and to this solution was added 170 μl. (1.21 mmol.) of triethylamine in 3 ml. of THF.

To the Boc-Gly-OSu solution was added under ice-cooling the thyroxine methyl ester solution. The resulting mixture was allowed to stand to reach room temperature, and then stirred for 1.5 hrs. The reaction liquid was allowed to stand overnight, and to this were added 25 ml. of distilled water and 50 ml. of ethyl acetate for extraction with the ethyl acetate. The extraction with 25 ml. of ethyl acetate was repeated three times. The ethyl acetate extracts were combined and dried over anhydrous magnesium sulfate. The dry extract was concentrated in a rotary evaporator and subjected to gel chromatography using a column filled with Sephadex LH-20 (tradename of Pharmacia Corp.). In this procedure, a mixture of acetone and methanol in a volume ratio of 4:1 was employed as the developing solvent. Under confirmation by TLC, the fractions containing the desired product were collected and concentrated under reduced pressure to obtain a crystalline product. There was obtained 950 mg. (yield 82.5%) of the desired product.

(2) Removal of BOC 950 mg. (1 mmol.) of Boc-Gly-T$_4$-OCH$_3$ prepared in the above (1) was dissolved in 10 ml. of trifluoroacetic acid. The resulting mixture was stirred for 10 min. under ice-cooling, and subjected to evaporation under reduced pressure at a temperature of below 40° C. The residue was subjected to gel chromatography under the same conditions as in the above (1) to collect fractions containing the desired product. Upon crystallization, there was obtained 700 mg. (yield 82.5%) of the desired product.

(3) Preparation of fluorescein isothiocyanic acid glycylthyroxine methyl ester (FITC-Gly-T$_4$-OCH$_3$)

320 mg. (0.33 mmol.) of Gly-T$_4$-OCH$_3$ trifluoroacetic acid salt obtained in the above (2) and 47 μl. (0.33 mmol.) of triethylamine were dissolved in 5 ml. of methanol. The resulting solution was added to 130 mg. (0.33 mmol) of FITC in 45 ml. of methanol. After reaction was carried out for 24 hrs. at room temperature, the solvent was removed under reduced pressure at a temperature below 40° C. The residue was saponified in a mixture of an alkali and methanol, neutralized, and evaporated to dryness. The resulting residue was then subjected to gel chromatography under the same conditions as in the above (1) to collect fractions containing the desired product. Upon crystallization, there was obtained 290 mg. (yield 70%) of an orange colored crystalline product.

B. Preparation of Anti-Thyroxine Serum (1) Preparation of N-methyl-N-carboxymethyl glycylthyroxine methyl ester (T$_4$-MEMIDA)

In 15 ml. of dimethylformamide (DMF) was dissolved 2 g. of thyroxine methyl ester hydrochloride, and to this was added 500 μl. of triethylamine. After 10 min., 0.55 g. of N-methyliminodiacetic acid in 5 ml. of THF was added to the resulting solution. This reaction mixture was concentrated in a rotary evaporator, and a residue was dissolved in 50 ml. of THF. After addition of 150 ml. of ethyl acetate, the mixture was shaken. The ethyl acetate phase was taken up and washed successively with three portions of distilled water and one portion of a saturated aqueous saline solution. The ethyl acetate phase was dried over anhydrous sodium sulfate, and the supernatant was concentrated in a rotary evaporator. To the residue were successively added 20 ml. of THF and a small amount of n-hexane. The produced precipitate was collected by filtration with suction to obtain a white crystalline product. The product was dried in a vacuum desiccator to give white crystals; yield 69%.

(2) Preparation of anti-thyroxine serum

In 2.0 ml. of dry DMF was dissolved 100 mg. of T$_4$-MEMIDA prepared in the above (1). To the resulting solution were added successively 15 mg. of N-hydroxysuccinimide and, with ice-cooling, 25 mg. of 1-ethyl-3-(3-dimethylaminopropyl)carbodiimide (ECDI). The mixture was kept overnight at 4° C. for carrying out a reaction.

The solution prepared as above was dropped with ice-cooling into 20 ml. of 0.05M aqueous carbonate buffer solution (pH 9.0) containing 100 mg. of bovine serum albumin (available from Miles Laboratories Inc., USA, Fraction V), and a reaction was effected. The reaction liquid was dialyzed for two days against the same buffer solution (2 l.×4 times) so as to remove an unreacted substance. The reaction liquid was further dialyzed for two days against distilled water (2 l.×4 times) for desalting, and then freeze-dried. The freeze-dried product amounted to approx. 130 mg. This product was identified as a bovine serum albumin containing approx. 20 haptens per one bovine serum albumin molecule, according to IR spectrum determination.

The so freeze-dried product was introduced into a rabbit for immunological treatment in a conventional manner to give an anti-thyroxine serum.

EXAMPLE 1

A FITC-Gly-T$_4$ solution was prepared by dissolving the FITC-Gly-T$_4$ in 0.3M aqueous glycine-sodium hydroxide buffer solution (pH 9.0) in 0.1 μM concentration.

100 μl. of the anti-thyroxine serum was diluted with 19.9 ml. of 0.02M aqueous phosphate buffer solution (pH 7.3) containing 0.3% of bovine serum albumin and 0.15M sodium chloride to prepare an anti-thyroxine serum solution.

1 ml. of human serum (Consera: trademark of Nissui Pharmaceutical Co., Ltd., Japan) was diluted with 9 ml. of 0.02M aqueous phosphate buffer solution (pH 7.3, same below) containing 0.15M sodium chloride to prepare a serum solution.

The compounds listed below were dissolved in water or an alkaline solution to obtain a 1 wt. % solution and evaluated for the activity as the blocker.

Compound 1: Thimerosal
Compound 2: Sodium salicylate
Compound 3: 1-Anilino-8-naphthalenesufonic acid (ANS)
Compound 4: Aforementioned compound (1a)
Compound 5: Aforementioned compound (3a) in which the oxyethylene groups were 2-4 units (mixture)
Compound 6: Aforementioned compound (16a)
Compound 7: Aforementioned compound (17a)
Compound 8: Aforementioned compound (8a)
Compound 9: Aforementioned compound (18b)
Compound 10: Aforementioned compound (18a)
Compound 11: Aforementioned compound (5a)
Compound 12: Aforementioned compound (5b)
Compound 13: Aforementioned compound (1b)
Compound 14: Aforementioned compound (6a)
Compound 15: Aforementioned compound (14c)
Compound 16: Aforementioned compound (15a)

Evaluation of blocking activity

Into a test tube, 250 μl. of FITC-Gly-T$_4$, 100 μl. of the serum solution, 100 μl. of a solution of the abovementioned compound (blocker solution), and 550 μl. of 0.3M aqueous glycine-sodium hydroxide solution (pH 9.0) were introduced to prepare totally 1 ml. of a test liquid. The test liquid was sufficiently mixed under stirring and allowed to stand for approx. 10 min. at room temperature. The fluorescence strength of the test liquid was then measured at an exciting wavelength of 492 nm and a measuring wavelength of 525 nm in a fluorometer 650-10 (available from Hitachi Ltd., Japan). The measured value was named "Hs fluorescence strength".

The procedure described as above was repeated except for replacing the serum solution with the same amount of the anti-thyroxine serum solution to prepare a test liquid. The resulting test liquid was subjected to fluorometry in the same manner as above. The so measured value was named "Ab fluorescence strength".

The same procedure was further repeated except for replacing the blocker solution with the same amount of PBS to prepare a control liquid. The resulting control liquid was then subjected to to the same fluorometry.

The fluorescence strength values obtained in the measurements are set forth in Table 1, in which the values are given in terms of relative values to the value measured in the measurement of Ab fluorescence strength in the case of employing the above-identified compound-7. Thus, the value on the compound-7 is expressed by 100.

TABLE 1

| Compound | Fluorescence Strength | | |
| --- | --- | --- | --- |
| No. | Ab | HS | Ab - Hs |
| 1 | 99 | 88 | 11 |
| 2 | 105 | 86 | 19 |
| 3 | 86 | 42 | 44 |
| 4 | 107 | 43 | 64 |
| 5 | 106 | 40 | 66 |
| 6 | 101 | 40 | 61 |
| 7 | 100 | 40 | 60 |
| 8 | 106 | 44 | 62 |
| 9 | 104 | 44 | 60 |
| 10 | 107 | 46 | 61 |
| 11 | 100 | 43 | 57 |
| 12 | 108 | 48 | 60 |
| 13 | 107 | 49 | 58 |
| 14 | 112 | 63 | 49 |
| 15 | 105 | 41 | 64 |
| 16 | 102 | 50 | 52 |
| Control | 106 | 116 | (—)10 |

Remark: The concentration of the compound in the test liquid was adjusted to approx. 0.1% (wt./vol.).

Blank liquids containing the above-identified compounds were prepared by the same procedure as described above except for replacing the serum solution or anti-thyroxine solution with the same amount of PBS. These blank liquids were treated in the same manner and subjected to the same fluorometry. The measured values all amounted to approx. 42 (in terms of the relative value, as in Table 1).

The fluorescence strength values shown in Table 1 are thought to mean the following.

The FITC of FITC-Gly-$T_4$ introduced into the test liquid is apt to be quenched by iodine. In the case where the FITC is bound to thyroxine containing four iodine atoms, the FITC shows a relatively low fluorescence strength because FITC and thyroxine are present in positions spatially adjacent to each other (as seen from the fluorescence strength on the above-mentioned blank liquid).

When an anti-thyroxine serum (antibody) is introduced into the FITC-Gly-$T_4$ solution, most of the thyroxine ($T_4$) molecules are combined with the newly introduced anti-thyroxine serum, so that the positions of the fluorescent compound (FITC) and thyroxine are made far away from each other. Thus, in such a case, the distance between FITC and $T_4$ in the FITC-Gly-$T_4$ complex increases due to change of their spatial positions, and the quenching effect of iodine given to the FITC is rendered weaker. Accordingly, the fluorescence strength of the solution increases, as seen from the Ab fluorescence strength on the control liquid.

Further, in the case where a serum containing a thyroxine-binding protein is introduced into a FITC-Gly-$T_4$ solution, most of the thyroxine ($T_4$) molecules are bound by the protein so that the fluorescent compound (FITC) is difficultly affected by the quenching power of iodine. Accordingly, the fluorescence strength of the solution increases, as seen from the Hs fluorescence strength on the control liquid.

In contract, if a blocker showing high blocking activity is present in a FITC-Gly-$T_4$ solution into which a serum containing a thyroxine-binding protein is introduced, the blocker is predominantly bound by the protein. Accordingly, most of the thyroxine ($T_4$) molecules of the FITC-Gly-$T_4$ are hardly affected by the presence of such a protein, and these thyroxine molecules are kept at their original positions spatially adjacent to the fluorescent compound (FITC). For this reason, the fluorescence strength of the solution is almost equal (meaning almost no change) to or only slightly higher than the fluorescence strength obtained in the liquid containing no serum solution (in this example, corresponding to the value on the above-mentioned blank liquid, namely, approx. 42). On the contrary, if the blocker employed shows merely low blocking activity, not a few proteins in the serum binds the thyroxine instead of the blocker. Accordingly, the thyroxine molecule moves to a position spatially far from the fluorescent compound (FITC), and the influence of thyroxine given to the FITC is rendered weaker. Thus, the fluorescence strength of the solution increases.

Accordingly, it is understood from the present example that a bloker is regarded as having high blocking activity if the Hs fluorescence strength of a test sample containing said blocker is near 42 (fluorescence strength of the blank liquid). On the other hand, if the Hs fluorescence strength of a test liquid containing a blocker is near 116 (fluorescence strength of the control liquid), said bloker is regarded as having low blocking activity.

In this example, the influences of the blocker and the anti-thyroxine serum given to the fluorescence strength of the FITC-Gly-$T_4$ solution were independently measuerd for each of the blockers, and then differences between the so obtained Ab fluorescence strength and the Hs fluorescence strength (Ab-Hs) were calculated to evaluate more accurately on the blocking activity of these blockers. Thus, the value given in the column Ab-Hs in Table 1 is understood to mean a value indicating a blocking activity obtained by removing the background value, and therefore a high Ab-Hs value means more accurately a high blocking activity.

In addition, the results of the evaluation on the blocking activity of the blockers given in this example (Example 1) were confirmed as having close relationship with the results of evaluation of these blockers in application to homogeneous enzyme immunoassay described in Example 4 given hereinafter.

EXAMPLE 2

Evaluation of blockers by fluorometry (Evaluation of blockers in liquid sample containing serum in high concentration)

800 μl. of 0.3M aqueous glycine-sodium hydroxide solution (pH 9.0) was taken up into a test tube, and the content was evaporated to dryness.

Into the above test tube were introduced 800 μl. of a human serum (Consera: trademark of Nippon Seiyaku Co., Ltd., Japan), 50 μl. of FITC-Gly-$T_4$ solution containing 0.5 μM FITC-Gly-$T_4$ dissolved in 0.3M aqueous glycine-sodium hydroxide buffer solution (pH 9.0), 50 μl. of a blocker solution containing 50 mM blocker (compound set forth in Table 2) dissolved in 0.25M aqueous sodium hydroxide solution, and 100 μl. of the anti-thyroxine serum, to prepare totally 1 ml. of a test liquid.

The test liquid was sufficiently mixed under stirring and allowed to stand for approx. 10 min. at room temperature. The fluorescence strength of the test liquid was then measured at an exciting wavelength of 492 nm and a measuring wavelength of 525 nm in a fluorometer 650-10 (available from Hitachi Ltd., Japan). The measured value was named "Hs-As fluorescence strength".

The same procedure was repeated except for replacing the anti-thyroxine serum solution with the same amount of PBS to prepare a test liquid. The resulting test liquid was then subjected to the same fluorometry. The measure value was named "Hs-PBS fluorescnece strength".

The fluorescence strength values obtained in the measurements are set forth in Table 2, in which the values are given in terms of relative values to the value measured in the measurement of Ab fluorescence strength in the case of employing the above-identified compound-7. Thus, the value on the compound-7 is expressed by 100.

TABLE 2

| Compound No. | Fluorescence Strength | | |
|---|---|---|---|
| | Hs-Ab | HS-PBS | Hs-Ab - Hs-PBS |
| 2 | 77 | 77 | 0 |
| 3 | 76 | 74.5 | 1.5 |
| 4 | 65 | 57 | 8 |
| 5 | 66 | 55.5 | 10.5 |
| 6 | 66.5 | 46 | 20.5 |
| Control | 82 | 46 | (−)2 |

Remark: The compound No. given in Table 2 corresponds to the compound No. described in Example 1.

As for the difference between the Hs-Ab fluorescence strength and the Hs-PBS fluorescence strength (As-Ab-Hs-PBS), a higher value means a higher blocking activity, for the similar reason described in Example 1.

EXAMPLE 3

Evaluation of blockers by fluorometry (Preparation of calibration curves of thyroxine in the presence of blockers)

Into a test tube were introduced 250 μl. of FITC-Gly-$T_4$ solution containing 0.1 μM FITC-Gly-$T_4$ dissolved in 0.3M aqueous glycine-sodium hydroxide buffer solution (pH 9.0), 100 μl. of the anti-thyroxine serum diluted 200 times with PBS containing 0.3% bovine serum albumin, 450 μl. of 0.3M aqueous glycine-sodium hydroxide buffer solutin, 100 μl. of a blocker solution containing 1% (wt./vol.) of a blocker (compound set forth below) dissolved in 0.25M aqueous sodium hydroxide solution, and 100 μl. of the human serum containing different concentration of thyroxine, to prepare totally 1 ml. of a test liquid.

The test liquid was sufficiently mixed under stirring and allowed to stand for approx. 10 min. at room temperature. The fluorescence strength of the test liquid was then measured at an exciting wavelength of 492 nm and a measuring wavelength of 525 nm in a fluorometer 650-10 (available from Hitachi Ltd., Japan).

The above-mentioned serums were employed after removal of a body fluid origin thyroxine originally contained therein by the use of active carbon in the manner provided by Mitsuma, et al. in T. Mitshuma, J. Colucci, L. Shenkman & C. S. Hollander: Biochemical and Biophysical Research Communications, 46, 2107–2113 (1972).

Calibration curves were prepared by plotting the fluorometrically measured values against the horizontal line indicating the final concentration of thyroxine in the test liquid. The fluorometrically measured values were given as relative values to the value measured in 2 μg./dl. of final thyroxine concentration (which was set to 100).

Figure 1:
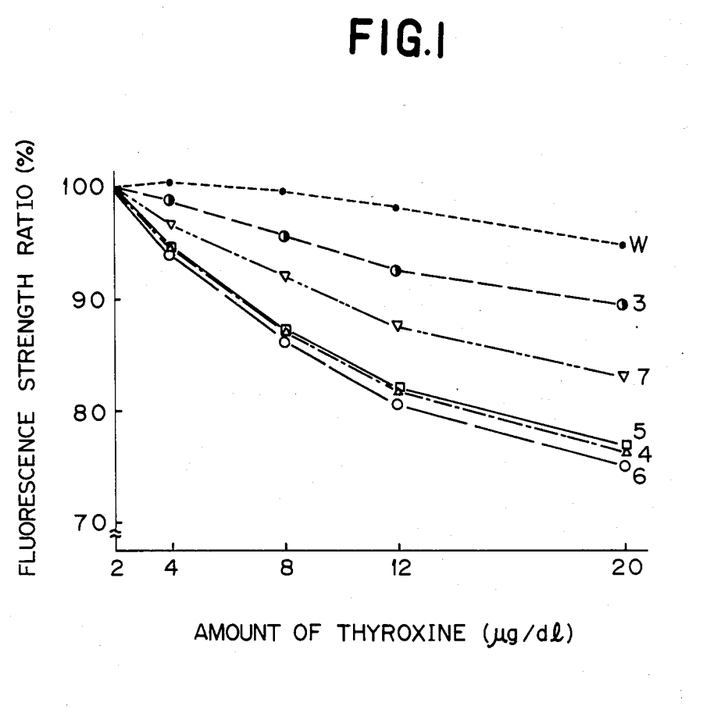
FIG. 1 shows examples of calibration curves adaptable for quantitative fluorometry of thyroxine in the presence of different blockers in which a curve indicated by W is a control curve employing no blocker, a curve indicated by 3 is a comparative curve employing the known ANS blocker, and curves indicated by 4 through 7 are curves employing blockers according to the present invention.

The so prepared calibration curves are given in FIG. 1. The curves correspond to the blockers as follows, in which the compound No. is identical to that given in Example 1:

Compound 3 (ANS): Calibration curve 3
Compound 4: Calibration curve 4
Compound 5: Calibration curve 5
Compound 6: Calibration curve 6
Compound 7: Calibration curve 7
Water (Control): Calibration curve W FIG. 1 indicates that the calibration curves corresponding to the test liquids containing the compounds (Compounds 4 through 7) included in the present invention have broad measurement ranges. In the measuring system, the broad measurement range enables to carry out an accurate measurement.

EXAMPLE 4

Application to homogeneous enzyme immunoassay (1) Preparation of complex of thyroxine and malate dehydrogenase In 200 μl. of dry dimethylformamide was dissolved 10 mg. of $T_4$-MEMIDA, and to the resulting solution were successively added 1.5 mg. of N-hydroxysuccinimide and, under ice-cooling, 2.5 mg. of 1-ethyl-3-(3-dimethylaminopropyl)carbodiimide. The mixture was then reacted overnight at 4° C. to prepare an active ester solution.

Independently, 25 mg. of malate dehydrogenase (MDH, hog myocardium mitochondria origin, available from Boehringer Mannheim A. G., West Germany) was dissolved in 5 ml. of 0.05M aqueous sodium carbonate buffer solution (pH 9.2), and to this solution was added under ice-cooling the above active ester solution in a rate of 10 μl./min. After the addition was complete, the reaction liquid was stirred for 2 hours under ice-cooling. The reaction liquid was then subjected to gel-filtration using Sephadex G-50 (trademark, available from Farmacia Corp.) to obtain an MDH fraction. The obtained MDH fraction showed an enzymic activity 0.1–0.2 time as much as that of the original MDH.

(2) Preparation of human serum

To human serums obtained by removing a body fluid origin thyroxine from the serum by the use of active carbon in the manner of Mitsuma et al. described in Example 3 were added thyroxines to give solutions of different concentrations, namely, 5, 10, and 20 μg./dl. to prepare thyroxine-containing human serums.

(3) Application to homogeneous enzyme immunoassay

In a test tube was taken up 50 μl. of the above-obtained human serum. To this serum was added 50 μl. of a solution of 0.3M aqueous glycine-sodium hydroxide buffer solution (pH 9.0) containing 5 mM of the below-mentioned blocker. The resulting mixture was stirred and allowed to stand for approx. 10 min. at room temperature. To this was added 1 ml. of 0.15M aqueous glycine-hydrochloric acid buffer solution (pH 5.5) containing 2 μl. of the anti-thyroxine serum and 80 mg. of β-NAD (β-nicotinamideadeninedinucleotide). The resulting mixture was stirred and allowed to stand for approx. 5 min. at room temperature. To this was further added 550 μl. of 0.3M aqueous glycine-sodium hydroxide buffer solution (pH 9.3) containing 0.3M L-malic acid to make the total amount to 650 μl., and the mixture was stirred sufficiently.

The so obtained solution was subjected to photometric measurement for determining variation of absorbance at a wavelength of 340 nm in UV-240 photometer (available from Shimadzu Seisakusho Ltd., Japan).

Figure 2:
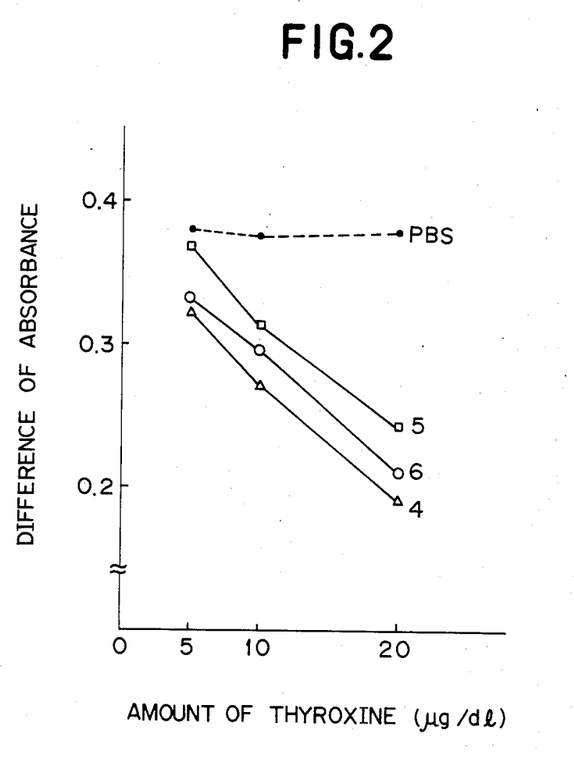
FIG. 2 shows examples of response curves of thyroxine in varying amounts in the presence of different blockers in a homogeneous enzyme immunoassay.

The difference in the absorbance between at the beginning and at lapse of 15 min. is plotted to provide a graph illustrated in FIG. 2.

The blockers and the response curves corresponding to the blockers are as follows, in which the compound No. is identical to that given in Example 1.

Compound 4: Response curve 4
Compoumd 5: Response curve 5
Compound 6: Response curve 6
PBS (control): Response curve PBS FIG. 2 indicates that the response curves corresponding to the test liquids containing the compounds (Compounds 4 through 6) included in the present invention have broad measurement ranges, that is, high response can be observed to correspond to the amount of thyroxine. In the measuring system, the broad measurement range enables to carry out an accurate measurement. Accordingly, the blockers included in the present invention are satisfactorily employable in quantitative analysis in a homogeneous enzyme immunoassay, because these blockers effectively serve for providing highly quantitative results without disturbing the enzymic activity.

We claim:

1. A method for quantitative analysis of thyroid hormone in a protein-containing liquid sample originating from body fluids and wherein said thryoid hormone is capable of binding to said protein, comprising liberating said hormone from said protein by incorporating into the liquid sample a compound having the formula (I):

$$X-(Y)_p-SO_3M \qquad (I)$$

in which M is hydrogen ion, an alkali metal ion, or ammonium ion; X is a straight or branched alkyl, alkenyl, fluorinated alkyl, or fluorinated alkenyl group containing at least 6 carbon atoms, Y is a divalent organic residue; and p is 0 or 1.

2. The method for quantitative analysis of thyroid hormone as claimed in claim 1, in which the quantitative analysis utilizes an antigen-antibody reaction.

3. The method for quantitative analysis of thyroid hormone as claimed in claim 1, in which the liquid sample is selected from the group consisting of blood, serum, plasma, urine, bone marrow fluid, saliva, and their processed products.

4. The method for quantitative analysis of thyroid hormone as claimed in claim 1, in which the protein is selected from the group consisting of albumin, globulin, and prealbumin.

5. The method for quantitative analysis of thyroid hormone as claimed in claim 1, in which X of the formula (I) is a straight or branched alkyl, alkenyl, fluorinated alkyl, or fluorinated alkenyl group containing 8-22 carbon atoms.

6. The method for quantitative analysis of thyroid hormone as claimed in claim 1, in which p of the formula (I) is 0.

7. The method for quantitative analysis of thyroid hormone as claimed in claim 1, in which p of the formula is 1 and Y of the formula (I) is a divalent organic residue containing a monovalent or divalent aromatic ring.

8. The method for quantitative analysis of thyroid hormone as claimed in claim 7, in which p of the formula is 1 and Y of the formula (I) is a divalent organic residue containing a monovalent or divalent benzene or naphthalene ring.

9. The method for quantitative analysis of thyroid hormone as claimed in claim 1, in which p in formula (I) is 1 and y is a divalent organic residue selected from the group consisting of

1.

2.

3. —(aromatic ring)—O—(OCH$_2$CH$_2$)$_m$—;

4.

5. —(aromatic ring)—Z—;
6. —NHCO—(aromatic ring)—Z—;
7.

8. —Z—O—;
9.

10. —NHCONH—(aromatic ring)—Z—;
11. —NHCSNH—(aromatic ring)—Z—;
12. —S—(aromatic ring)—Z—;
13. —O—Z—(aromatic ring)—;
14.

15.

16.

17.

wherein
the aromatic ring may contain one or more substituents, such as, hydroxy, alkoxy, aryloxy, alkyl, carbamyl, amido sufamido, halogen, carboxyl and sulfonyl;
m is an integer of 0 to 3;
n is an integer of 1 to 5;
A is hydrogen atom or a lower alkyl group;
D is hydrogen atom or a lower alkyl group;
Z is a simple bondong or a divalent organic residue; and
V is a monovalent organic residue.

* * * * *